(12) United States Patent
Hacker et al.

(10) Patent No.: US 12,295,885 B2
(45) Date of Patent: May 13, 2025

(54) ARRANGEMENT FOR THE OCT-BASED LASER VITREOLYSIS

(71) Applicant: Carl Zeiss Meditec AG, Jena (DE)

(72) Inventors: Martin Hacker, Jena (DE); Mark Bischoff, Jena (DE); Manfred Dick, Gefell (DE)

(73) Assignee: Carl Zeiss Meditec AG, Jena (DE)

( * ) Notice: Subject to any disclaimer, the term of this patent is extended or adjusted under 35 U.S.C. 154(b) by 49 days.

(21) Appl. No.: 17/766,607

(22) PCT Filed: Sep. 24, 2020

(86) PCT No.: PCT/EP2020/076674
§ 371 (c)(1),
(2) Date: Apr. 5, 2022

(87) PCT Pub. No.: WO2021/069220
PCT Pub. Date: Apr. 15, 2021

(65) Prior Publication Data
US 2024/0108506 A1 Apr. 4, 2024

(30) Foreign Application Priority Data
Oct. 9, 2019 (DE) .................. 10 2019 007 148.4

(51) Int. Cl.
*A61F 9/007* (2006.01)
*A61B 3/10* (2006.01)
(Continued)

(52) U.S. Cl.
CPC ............. *A61F 9/008* (2013.01); *A61B 3/102* (2013.01); *A61F 9/009* (2013.01); *A61F 2009/00874* (2013.01)

(58) Field of Classification Search
CPC ................ A61F 9/008; A61F 9/009; A61F 2009/00874; A61B 3/102
See application file for complete search history.

(56) References Cited

U.S. PATENT DOCUMENTS 9,474,649 B2 * 10/2016 Palanker ............. A61F 9/00836
11,364,147 B2 * 6/2022 Palanker ............. A61F 9/00754
(Continued)

FOREIGN PATENT DOCUMENTS

DE       10 2011 103 181 A1    12/2011

OTHER PUBLICATIONS

International Search Report for PCT/EP2020/076674, mailed Dec. 7, 2020, 3 pages.
(Continued)

*Primary Examiner* — Eric D. Bertram
(74) *Attorney, Agent, or Firm* — DeWitt LLP

(57) ABSTRACT

An arrangement for OCT-based laser treatment of vitreous floaters. The arrangement for OCT-based laser vitreolysis includes an OCT system, a laser system having a deflection unit, optical elements that couple the OCT system and the laser system, a display unit and a central control and operating unit. The OCT system is configured to localize the floaters, the laser system is configured to destroy the floaters by application of laser pulses and the central control and operating unit is configured to determine apart from the coordinates of the localized floaters also their distance to structures of the eye, to derive exclusion criteria for the treatment, to align the deflection unit of the laser system to these coordinates and to focus and activate the laser system. The present invention relates to an arrangement for the gentle, low risk and painless laser treatment of vitreous floaters, which enables partially or fully automated therapy.

24 Claims, 1 Drawing Sheet

(51) Int. Cl.
    *A61F 9/008*     (2006.01)
    *A61F 9/009*     (2006.01)

(56) References Cited

U.S. PATENT DOCUMENTS

| | | | |
|---|---|---|---|
| 2006/0195076 A1 | 8/2006 | Blumenkranz et al. | |
| 2011/0300490 A1* | 12/2011 | Rachet | G02B 26/0833 359/385 |
| 2013/0242259 A1* | 9/2013 | Hacker | A61B 3/102 351/246 |
| 2014/0153864 A1* | 6/2014 | Sinclair | G02B 6/262 385/12 |
| 2014/0246612 A1* | 9/2014 | Spiecker | G02B 27/144 359/227 |
| 2014/0257257 A1* | 9/2014 | Grant | A61F 9/00825 606/4 |
| 2015/0342782 A1* | 12/2015 | Mordaunt | A61F 9/00802 606/4 |
| 2015/0366712 A1* | 12/2015 | Palanker | A61F 9/0084 606/4 |
| 2017/0326003 A1* | 11/2017 | Schuele | A61F 9/00825 |
| 2018/0028354 A1 | 2/2018 | Heeren | |
| 2018/0207029 A1* | 7/2018 | Herekar | A61N 5/0625 |
| 2020/0038241 A1* | 2/2020 | Wang | A61F 9/009 |

OTHER PUBLICATIONS

English translation of International Search Report for PCT/EP2020/076674, mailed Dec. 7, 2020, 2 pages.

Brasse, K., Schmitz-Valckenberg, S., Jünemann, A. et al. Ophthalmologe (2019) 116: 73. https://doi.org/10.1007/s00347-018-0782-1).

Ellex (product brochure by Ellex Medical Pty Ltd.; "Tango Reflex—Laser Floater Treatment"; PB0025B; 2018; (http://www.ellex.com)).

* cited by examiner

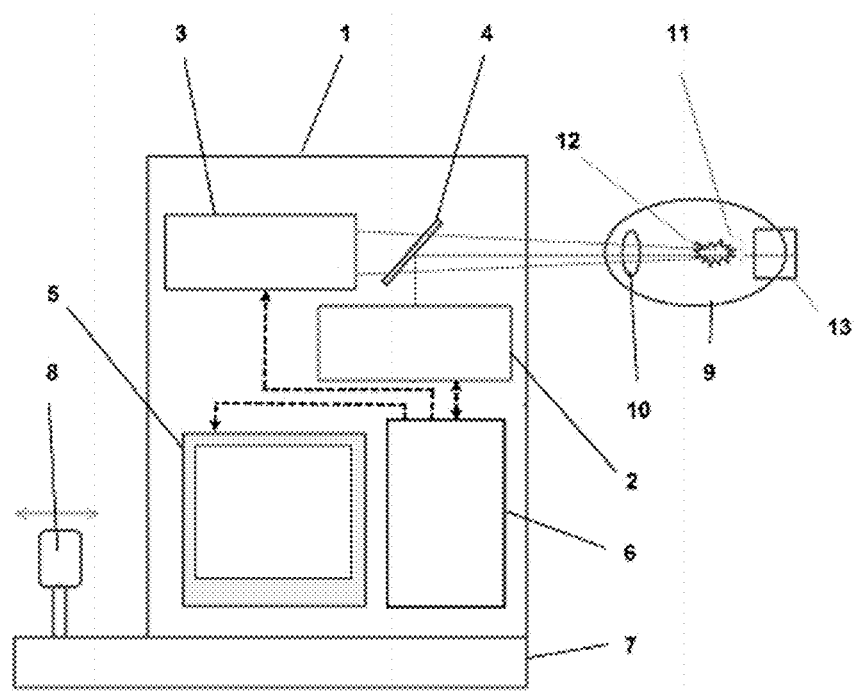

ARRANGEMENT FOR THE OCT-BASED LASER VITREOLYSIS

RELATED APPLICATIONS

This application is a National Phase entry of PCT Application No. PCT/EP2020/076674 filed Sep. 24, 2020, which application claims the benefit of priority to DE Application No. 10 2019 007 148.4 filed Oct. 9, 2019, the entire disclosures of which are incorporated herein by reference.

TECHNICAL FIELD

The present invention relates to an arrangement for treating vitreous humor opacification by laser with OCT assistance.

BACKGROUND

The vitreous humor consists of a usually clear, gel-like substance in the interior of the eye between the lens and the retina. In youth, the vitreous humor is completely clear and has contact with the retina. Over the course of a lifetime, the vitreous humor liquefies and increasingly detaches from the retina; this is referred to as posterior vitreous detachment. This is a normal aging process which usually occurs after the age of 50. The detached vitreous humor components come together in the interior of the eye and the framework substances and concentrations of the vitreous humor are rendered visible to the patients. Since they may also move across the visual field, they are also referred to as floaters. Often, as a cause of floaters, membrane-like structures are also present on the posterior side of the vitreous humor following the vitreous humor detachment, sometimes even the remains of blood should retinal injury have occurred during the vitreous humor detachment. In rare cases, floaters may also be present as crystal-like precipitates in the vitreous humor in the case of metabolic problems.

Even if floaters usually do not have a pathological cause, they are not as harmless as generally assumed because they can impair, sometimes significantly impair, the quality of life and also work productivity of the affected parties.

This opacification is perceived especially against a bright background, for example when working on a computer, when reading or when looking at the blue sky or snow, and disturbs the visual faculty. Floaters that are flung into and out of the central field of vision as a result of the reading movements when reading can be particularly bothersome.

Since these often have the form of a "flying gnat", they are described using the technical term "mouches volantes"—which comes from the French. However, the opacification may also have different shapes, for example be branch-, ring- or star-shaped, or else be present as point clouds. In the following text, the term "floater" is used for the vitreous humor opacification to be treated, irrespective of its type or form.

In general, floaters do not disappear without treatment because the immune system does not recognize these as abnormal and therefore does not destroy these. However the affected parties can hardly ignore or overlook them. Certain floater types, such as those caused by residual blood following retinal bleeding, are partly resorbed by the body again, even if this takes weeks or months.

In what is known as vitrectomy, the vitreous humor is partly (core vitrectomy) or completely comminuted, aspirated and removed after the eye has been opened up using cutting tools. Such an intervention is carried out routinely in the case of retinal detachments or the peeling of epiretinal membranes, but is usually considered a disproportionate therapy for removing the localized vitreous humor opacification. Moreover, vitrectomy is invasive, requires a stay at a clinic and harbors the risks linked to surgical interventions, in particular the frequent inducement of a cataract, seldom a retinal detachment and very seldom, but possible, endophthalmitis.

So-called laser vitreolysis now offers a low-risk treatment alternative. Laser vitreolysis is a sparing, low-risk and pain-free laser treatment, by application of which the vitreous humor opacification can be vaporized or atomized without opening up the eye.

In the case of laser vitreolysis, short laser light pulses are directed at the vitreous humor opacification in order to obtain optical breakdown or photodisruption there on account of the high laser intensity in the focal region. The floaters and the vitreous humor surrounding these absorb the laser energy and a cutting or expanding laser plasma is formed, as a result of which the floaters are vaporized and/or comminuted and can as a result dissolve. The treatment causes little pain and is without risk of infection. Laser vitreolysis provides a safe method for the sparing treatment of bothersome vitreous humor opacification should it be possible to ensure that important and sensitive eye structures, for example the capsular bag, the crystalline lens or retinal regions, especially the macula, are not damaged by the laser.

However, the success of the treatment depends on the type of floater. The treatment is particularly successful in the case of so-called Weiss rings. Tissue strands can be severed and the tissue concentrations responsible for the disturbing shadows can be eradicated.

Floaters have been treated with YAG lasers for already more than three decades (Brasse, K., Schmitz-Valckenberg, S., Jünemann, A. et al. Ophthalmologe (2019) 116: 73. https://doi.org/10.1007/s00347-018-0782-1). However, only the most anterior region of the vitreous humor can be treated with precision and reliable targeting, even when the current high-end devices are used. These lasers are not precise enough in the deeper vitreous humor region. However, most vitreous humor opacification is found there as this often is the result of posterior vitreous humor detachment.

According to the known prior art, there are already numerous solutions for carrying out laser surgery on the tissue of the eye, especially in the vitreous humor.

Thus, DE 10 2011 103 181 A1 describes an apparatus and a method for femtosecond laser surgery on tissue, especially in the vitreous humor of the eye. The apparatus consists of an ultra short pulse laser with pulse lengths ranging from approximately 10 fs-1 ps, in particular of the order of 300 fs, pulse energies ranging from approximately 5 nJ-5 µJ, in particular approximately 1-2 µJ, and pulse repetition rates of approximately 10 kHz-10 MHz, in particular 500 kHz. The laser system is coupled to a scanning system which facilitates the spatial variation in the focus in three dimensions. In addition to this therapeutic laser scanner optics system, the apparatus furthermore consists of a navigation system coupled therewith.

US 2006/195076 A1 describes a system and method for producing incisions in ocular tissue at various depths. The system and the method focus light, possibly in a pattern, on different foci situated at different depths within the ocular tissue. A plurality of foci can be created simultaneously by way of a segmented lens. Optimal incisions can be obtained by virtue of the light being focused at different depths, either successively or simultaneously, and an extended plasma column and a beam with a lengthened waist being generated. The techniques described in this case can also be used, inter alia, to perform novel ophthalmological methods or to improve existing methods, including dissection of tissue in the posterior pole, for example floaters, membranes and the retina.

US 2014/257257 A1 also describes a system and its method for treating target tissue in the vitreous humor of an eye, comprising a laser unit for producing a laser beam and a detector for producing an image of the target tissue. The system also contains a computer which defines a focal spot path for emulsifying the target tissue. A comparator connected to the computer then controls the laser unit in order to move the focus of the laser beam. This focus movement is carried out to treat the target tissue while deviations of the focus from the defined focus path are minimized.

US 2015/342782 A1 likewise relates to a system and a method for using a computer-controlled laser system, for carrying out a partial vitrectomy of the vitreous humor in an eye. Surgically, an optical channel through the vitreous humor is defined first. Vitreous-like and suspended depositions (floaters) in the optical channel are then ablated and removed from the optical channel (e.g., aspirated) in some cases. In some cases, a clear liquid can be introduced into the optical channel in order to replace the ablated material and thereby establish an unimpeded transparency in the optical channel. In general, the present invention relates to systems and methods for ophthalmological laser operations. In particular, the present invention relates to systems and methods for using pulsed laser beams for removing what are known as floaters.

US 2018/028354 A1 likewise describes a method and a system for an ophthalmological intervention in an eye. Unwanted features are identified on the basis of an image of at least a portion of the eye.

Unwanted features in the vitreous humor cavity are considered to be instances of vitreous opacification that impair sight, for example floaters. Once the floaters have been identified and localized, they are sighted by a physician and manually "shot" with laser pulses. The laser energy evaporates at least some of a vitreous-like opacity. This procedure is repeated until the opacification of the vitreous humor has been removed. The entire procedure is repeated for each instance of opacification in the vitreous humor until the liquid of the vitreous humor is considered to be sufficiently clear.

A method described by ELLEX (product brochure by Ellex Medical Pty Ltd.; "Tango Reflex—Laser Floater Treatment"; PB0025B; 2018; (http://www.ellex.com)) provides for the use of a pulsed nanosecond laser (YAG) in order to decompose vitreous humor opacification or completely remove the latter by transition into a gas. A pilot laser beam is used to sight the target area (floater), which is subsequently "shot" using one or more therapeutic laser pulses. In this case, both the pilot laser beam and the therapeutic laser pulse are manually triggered by the user. Such a manual laser treatment typically consists of two individual treatments, each having a duration of 20-60 minutes.

The use of laser energy within the scope of laser vitreolysis is non-invasive and avoids the disadvantages of surgical interventions, but is also linked to disadvantages and risks.

Thus, targeting the laser may be difficult. Since the physician observes the vitreous humor along the beam path, it may be difficult to determine the depth of the position of the retina, the depth of the opacification of the vitreous humor or other relevant features. As a consequence, there is the risk of the opacification of the vitreous humor being missed and/or the eye being injured.

In particular, the treatment of largely transparent floaters, which change in position and are difficult to recognize but nevertheless, as phase objects, are able to generate bothersome shadows on the retina, was found to be difficult.

The application of laser energy may also lead to an additional movement of the opacification of the vitreous humor, making the treatment even more difficult. Consequently, the physician realigns the laser after each application of laser energy. This may require much time. Therefore, a treatment with laser energy is complicated and causes stress, both for the patient and for the physician.

A further possible problem relates to incomplete vitreous humor detachment, which may lead to local vitreous traction right up to retinal detachment. Laser treatment in the vitreous humor can lead to changes to changes in the balance of forces in the vitreous body due to shockwaves propagating as a consequence of said treatment, and thereby for example cause tension on the retina.

Lastly, the treatment of those floaters situated in the vicinity of sensitive structures of the eye was also found to be particularly difficult. In this case, the laser radiation can lead to damage in the retina, the crystalline lens or the macula.

SUMMARY OF THE INVENTION

Example embodiments of the present invention for example enable the OCT-assisted laser treatment of vitreous humor opacification, which rectifies the disadvantages of the known technical solutions. The solution should facilitate a simpler, quicker and especially safer treatment of bothersome vitreous humor opacification by way of laser vitreolysis. Moreover, the solution should be easy to implement and economically cost-effective.

Example embodiments of the invention includes an arrangement for OCT-assisted laser vitreolysis consisting of an OCT system, a laser system with deflection unit, optical elements for coupling OCT system and laser system, a display unit and a central control and operating unit by virtue of the OCT system being designed to locate the floaters, the laser system being designed to destroy the floaters by application of laser pulses, and the central control and operating unit being designed to determine the coordinates of the located floaters, to correspondingly align the deflection unit of the laser system and to focus and activate the laser system.

Example configurations predominantly relate to the central control and operating unit which is designed, in particular, to also determine the distance of the localized floaters from structures of the eye in addition to the coordinates of said floaters and to derive exclusion criteria for the treatment.

Thus, it can be further designed to determine the type and/or geometry of the floaters in addition to the coordinates thereof, and to generate or chose application-specific irradiation patterns for the laser system therefrom.

For example, the central control and operating unit is able to determine changes in the structure of the eye closest to the located floater during the treatment and to derive abort criteria for the treatment.

In accordance with a further configuration, the central control and operating unit is designed to automatically trigger the laser treatment within a time period of <20 ms, for example <10 ms, in another example <5 ms, taking account of the derived exclusion criteria for the treatment and the generated or chosen application-specific irradiation patterns.

Example embodiments of the present invention relates to an arrangement provided for sparing, low-risk and pain-free laser treatment of vitreous humor opacification. A partly or completely automated therapy device (system) is proposed, in which an OCT system is used for navigation purposes in order to locate the floaters within the scope of the treatment and in order to assist the treatment thereby.

The above summary is not intended to describe each illustrated embodiment or every implementation of the subject matter hereof. The figures and the detailed description that follow more particularly exemplify various embodiments.

BRIEF DESCRIPTION OF THE DRAWING

The invention is described in more detail below on the basis of example embodiments. In this respect:

The FIGURE is a symbolic representation of a slit lamp, in which the arrangement according to the invention for OCT-assisted laser vitreolysis is integrated.

DETAILED DESCRIPTION

The arrangement for OCT-assisted laser vitreolysis according to the invention consists of an OCT system, a laser system with deflection unit, optical elements for coupling OCT system and laser system, a display unit and a central control and operating unit, wherein the OCT system is designed to locate the floaters, the laser system is designed to destroy the floaters by application of laser pulses and the central control and operating unit is designed to determine the distance of located floaters from structures of the eye in addition to the coordinates of said located floaters, to derive exclusion criteria for the treatment, to align the deflection unit of the laser system on these coordinates and to focus and activate the laser system. For example, the laser system comprises a motor-driven deflection unit for automated beam deflection (scanning) in up to three dimensions.

When the laser system is focused, a programmed focal displacement between target position and located floater is for example taken into account.

To also exploit the acoustic shockwave produced by the laser beam, an anterior position in relation to the floater is helpful and set in the user settings of the central control and operating unit.

According to the invention, the coordinates of the located floaters and their distance from the structures in the eye are determined by the central control and operating unit from the OCT recordings. To this end, the vitreoretinal interfaces are recorded by use of OCT recordings, for example over a visual field angle of more than 450 or more than 120°.

This predominantly serves to determine before a vitreous humor treatment (in particular, the floater laser treatment or else vitrectomy) whether there are regions that may be problematic in respect of the treatment because the detected floaters are too close to sensitive structures of the eye. Initially, a decision for or against the treatment is made on the basis of these recordings and other information (exclusion criteria).

The determined distances between located floater and structures of the eye, by way of the central control and operating unit, serve to derive exclusion criteria for the laser processing, namely should the distance between the located floater and the retina, fovea, lens or the like be too small so that a laser treatment may have bleeding, retinal lesions or even a retinal detachment as a consequence.

Furthermore, processing and exclusion zones can be determined from the coordinates of the located floaters.

Firstly, these serve to realize an automated optimization of the positioning of the processing laser focus. Secondly, processing is only permitted if the processing laser focus is situated outside of the exclusion zone.

While a distance <1.5 mm is sufficient as an exclusion zone in respect of the optical and acoustic wave load to be expected, a distance of <2-3 mm should be applied for sensitive areas of the eye.

The user can be warned (acoustically and/or optically) when the processing laser focus approaches the exclusion zone. Additionally, it is possible to recognize and display the approach of sensitive structures. However, the laser processing may also be aborted.

There are different forms of vitreous humor opacification, which can also be treated to different degrees of success.

So-called Weiss-ring floaters are relatively large, fibrous ring-shaped floaters which are usually situated at a safe distance from the lens and the retina of the eye. As a result, these floaters can be treated safely and effectively by laser vitreolysis.

Floaters in the form of fibrous strands frequently occur in relatively young people and are perceived as a collection of points or thread-like tissue. Depending on the size and positions, these floaters can also be treated by laser vitreolysis.

By contrast, diffuse (cloud-like) floaters are the consequence of natural aging. Although this type of floater can also be treated by laser vitreolysis, a number of treatments are often required for a satisfactory result.

According to a first example configuration, the central control and operating unit is additionally designed to determine the type and/or geometry of the floaters in addition to the coordinates thereof, and to generate or select application-specific irradiation patterns for the laser system therefrom.

Such floater types can be for example Weiss rings, which form by the vitreous humor detachment at the optic nerve head, membranes, which form on posterior interfaces of the vitreous humor following detachment from the retina, cloud crystal-like floaters as a consequence of metabolic problems, or else coagulated blood following retinal bleeding. The type of floater can be determined by way of OCT signal strength distribution, absorption (for example by determining a more significant reduction of the signals from posterior structures behind a blood clot), the size and shape, the position (for example proximity to the optic nerve head), mobility or else the reaction to laser processing.

In accordance with a second example configuration, the central control and operating unit is additionally designed to determine changes in the structure of the eye closest to the located floater during the treatment and to derive abort criteria for the treatment. By way of example, the closest structure can be the capsular bag or else the vitreoretinal interface.

According to the invention, an abort or continuation decision during the treatment is derived by a detection of the change of geometric conditions at the vitreoretinal interface.

Example criteria in this respect are:
 an increase (or a threshold being exceeded) in a local change in direction or curvature on the retinal surface,
 an increase (or a threshold being exceeded) in the angle between vitreous humor interface (or epiretinal membrane) and the retinal surface, exceeding a limit of a change in relative position within the retinal layers (e.g., local shift of a retinal region in the anterior direction), the onset of bleeding during the treatment as an abort criterion, the onset of a capsular bag rupture during the treatment, or the onset of an elevated intraocular pressure during the treatment.

In a particular example, the position of the floaters in relation to the sensitive structures of the eye are automatically detected from the OCT recordings. To this end, the distance between the posterior capsular bag and retinal structures is determined by use of the OCT system and is used to make a respective decision in respect of which is the closest sensitive structure that should be tracked by use of OCT.

Should the treatment be continued, OCT is used to track over the course of the treatment whether the treatment can be continued or has to be aborted.

In particular, deriving an abort criterion should prevent the mechanical balance of forces at the vitreoretinal interface from developing disadvantageously as a result of vitreal processing and from making subsequent retinal lesions or even a retinal detachment more probable.

In accordance with a third example configuration, the central control and operating unit is additionally designed to automatically trigger the laser within the treatment, taking account of the derived exclusion criteria for the treatment and the application-specific irradiation patterns that were generated or are to be chosen.

To prevent the located floater from moving out of the focal region of the processing laser, the processing laser is triggered according to the invention within the time duration of <50 ms, better <20 ms, for example <10 ms, in another example <5 ms following the laser focus being overlaid on the floater.

According to the invention, the optical elements for coupling OCT system and laser system are based on dichroic or polarization-sensitive components or use a geometric combination (pupil split). It is not preferred but possible for mirrors to be introduced into the beam path very briefly in order to facilitate a very quick switchover between processing laser and OCT beam, for example by use of a quickly rotating mirror with transmission windows. For example, the beam cross sections of OCT and of the laser prior to the overlay are chosen such that the numerical aperture of the OCT beam in the eye is smaller than that of the processing laser. An advantage of this setting is that the signal strengths in the OCT signal have a less pronounced change in the case of axial focal positions than in the case of other configurations of the numerical aperture.

The coupling by use of dichroic optical components is for example implemented by use of a notch filter which transmits the processing laser and reflects the OCT beam.

In the case of the geometric combination, the two beams are guided close next to one another, with the respective angle being considered accordingly when determining the distance to the focal position.

Eyepieces and/or a display are used as display unit.

In accordance with a fourth example configuration, the OCT system, the laser system with deflection unit, the optical elements for coupling OCT system and laser system, the display unit and the central control and operating unit are integrated in a slit lamp.

This is advantageous in that the user can use the slit lamp to observe the posterior part of the eye and can locate opacification in the vitreous humor.

In this respect, the FIGURE shows the symbolic representation of a slit lamp, in which the arrangement according to the invention for OCT-assisted laser vitreolysis is integrated.

Additionally integrated into the slit lamp 1 (merely represented by a box) are the OCT system 2, the laser system 3 with deflection unit, the dichroic optical element 4 for coupling OCT system and laser system, a visual display unit 5 and a central control and operating unit 6.

It is well known that the slit lamp 1 is arranged on a base unit 7 which can be positioned along the z-axis in relation to the eye 9 by way of a joystick 8.

In addition to the crystalline lens 10, a located floater 11 and the laser focus 12 are depicted in the eye 9. Since the retina in this case is the structure of the eye 9 closest to the located floater 11, this region (denoted by reference number 13) is examined in more detail by application of OCT during the treatment.

In addition to the located floater 11, application-specific irradiation patterns, exclusion criteria or abort criteria for the treatment, or else defined processing and exclusion zones, for example, could be displayed for the operator on the visual display unit 5.

The proposed arrangement provides for the use of an OCT system, which is based on a spectral domain method or a time domain method or else a swept source method. An OCT holoscopy system without a scanning system is also useful and provided for this use, in order to have available a dynamic position control for the laser beam focus in the vitreous humor without delay.

Here, according to the invention, an axial scan depth>1 mm, for example 4 mm, in tissue in the case of an axial resolution of less than 100 µm, preferably 5 µm, FWHM in tissue, and a centroid wavelength of 840 nm are provided according to the invention, and an A-scan rate of 10 to 100 kHz. For example, the system comprises z-tracking of retina or capsular bag, depending on which structure of the eye is closer to the located floater.

For a swept source system, a centroid wavelength in the range of 1000-1070 nm, in particular for example 1050 nm or 1060 nm, a scan rate of 1 kHz to 100 MHz (e.g., by application of Fourier domain mode locked (FDML) lasers or VCSEL lasers) for example. According to example embodiments of the invention, the system is combined with a YAG laser, notch layer system filter and, in the process, covers the whole eye with its scanning depth. The axial resolution of the SS-OCT is for example chosen in such a way that it corresponds to the Rayleigh length of the processing laser, or else is greater than two times to three times the Rayleigh length. Although a higher axial resolution is possible, it hardly permits a better floater treatment.

According to the invention, a time domain system with scanning reference arm is also applicable. Apart from the A-scan rate, the example parameters correspond to those of the SD-OCT. In this case, the A-scan rates lie in the order of a few kHz, in particular 2 to 4 kHz.

The respective path components in air and eye should be considered for all OCT variants and a corresponding position determination correction and optionally a group speed dispersion correction may be necessary.

To be able to detect floaters well, the systems according to the invention have a sensitivity of 85 dB, for example at least 90 dB, in at least one part of the A-scan. In a further example variant, the A-scans have at least a sensitivity of 90 dB and further for example sensitivities of more than 100 dB over the entire scanning depth. Above approximately 90 dB, normal scattering on the vitreous humor and also on the crystalline lens becomes detectable even in regions without floaters, and thus allows the distinction of lens and vitreous humor structures from liquid-filled pockets or eye regions.

Independently of the variants just mentioned above, the OCT system can be designed as a one-, two- or else three-dimensionally scanning system, the functionality of the arrangement according to the invention varying on the basis of the scanning mode.

The position of the floater in the eye (in the coordinate system of the patient's eye) can be determined by application of a one-dimensional OCT scan (A-scan) and the distance of said floater from the retina or other interfaces can be calculated. This therefore serves to assist navigation and increase safety in the case of a manual treatment of the floaters. Additionally, a distance display for the user is rendered possible by realizing a processing zone, which delimits the extent of permitted processing. If the treatment laser is activated outside of the processing zone, i.e., in an exclusion zone, the user is warned and/or the output of therapy radiation is blocked.

Additionally, the approach of sensitive structures can be recognized and displayed by application of two-dimensional OCT scans (B-scans). Moreover, automatic tracking of a floater identified as such by the user is possible by use of a pilot laser beam. In this case, too, the processing laser still is activated by the user, who retains visual control and the ultimate decision.

Three-dimensional OCT scans (volume scans) allow the realization of an automated treatment of floaters within a zone specified by the user, which excludes an exclusion zone, an automated guidance of a treatment laser beam from floater to floater, and a confirmation of the target by the user. As a result, an automated, fast and secure treatment of vitreous humor opacification is carried out.

In a possible but not preferred variant, scans of a constant reference arm length, that is to say at a constant sample depth, can also be carried out by time domain OCT (C-scans).

According to the invention, the OCT system has a sensitivity of 90 dB, at least in a part of the A-scan. The proposed arrangement provides for the use of a laser system which is based on a μs to ns YAG laser, a ps- or an fs-laser.

While a pulse duration of 1-5 ns is useful according to the invention for a YAG laser, these durations are between 1 and 1000 ps in the case of a ps laser and between 50 and 1000 fs in the case of an fs laser.

Instead of YAG lasers such as the Nd:YAG laser at 1064 nm, 946 nm, 1320 nm wavelength, similar lasers such as for example the Nd:YLF laser at 1047 to 1053 nm and otherwise similar parameters as the YAG lasers can be considered. The use of frequency-doubled lasers is possible as a matter of principle, but the inexpediently amplified absorption by blood, in particular in vessels, needs to be considered.

According to one further example configuration, the laser system, in addition to a treatment beam, comprises at least one pilot beam for monitoring the correspondence of treatment beam focus and target area. Laser diodes in the VIS are suitable to this end, for example in the red spectral range.

In particular, the pilot beam can be continuous or quasi-continuous.

In the case where visual monitoring should be implemented by the user, it is helpful to use a pilot beam in the visible spectral range.

Moreover, it is possible to use a pilot beam in the visible or infrared spectral range in order to allow the detection system to capture and display scattered radiation arising at the floater. The simultaneous detection of the scattered light of the pilot beam of the laser system and optionally also of the processing pulse directly within the detection of the OCT system is particularly useful, in order to register both systems spatially accurately without further measures.

According to a further example configuration, the difference in the wavelengths of OCT and laser systems is less than 50 nm, for example less than 5 nm, so that common beam guidance and focusing elements can be used in the therapy device, but also so that the refraction of the light of both systems into the eye by way of corneal and lens refraction do not change significantly in relation to one another.

It was also found to be particularly helpful if the arrangement additionally comprises a tracking unit for tracking the irradiation pattern, in order to display the tracking of the irradiation pattern in the eyepieces and/or on the display.

This is particularly helpful if the located floater is a moving floater. Then, the galvano-mirror, for example, can be driven by the central control and operating unit, and dynamic focusing can be realized.

In this case, the automatic tracking following an image recognition for determining the coordinates of a recognized floater can be implemented in such a way that feedback to the user is overlaid, either in the display or in the eyepiece, or provided by use of a target beam.

Furthermore, it is according to the invention if the arrangement comprises an additional fixation mark for the patient, in order to facilitate advantageous or deliberate positioning of the patient's eye.

Moreover, a fixation mark for the patient offers the option of processing during voluntary or involuntary eye movements. By way of example, this may also be necessary in order to even bring floaters into the region accessible to processing. Additionally, a moving target mark can prompt the patient to move the eye in order to move floaters into or out of a region. By way of example, the degree of subjective interference by a floater can be checked by virtue of the floater being moved into the central visual range (e.g., in front of the macula), but then being moved into a region less critical to the laser processing, for example in front of the retinal periphery, and being subject to laser therapy there.

According to a last example configuration, the use of an additional vacuum contact glass for additional fixation of the eye is provided. In this case, an optional vacuum supply and coupling to the therapy laser during the treatment are provided. This is especially advantageous for example for highly precise laser treatment of floaters by application of fs lasers with focal diameters of less than 20 μm, 10 μm or even 5 μm. However, a vacuum contact glass for stabilizing the eye may be helpful for a treatment by application of YAG lasers as well. For the higher lateral resolutions, a pupil dilation and optionally also beam shaping by utilization of adaptive optics, for example deformable mirrors or else liquid crystal SLMs, are advantageous.

Moreover, treatment planning is possible with a proposed arrangement for OCT-assisted laser vitreolysis, by virtue of, prior to the treatment, floaters being "mapped". Then, a treatment sequence can be defined in order to select floaters to be treated, or to confirm these. Consequently, defining the treatment sequence from posterior to anterior or else along the posterior vitreous humor boundary is also possible in automated fashion.

Then, evidence about the treatment success can also be provided for the "mapped" floaters. To map the floaters that are movable to a certain degree, it is helpful to characterize the floaters not by way of their absolute position but by way of their neighborhood relationships and to update the latter after individual treatment steps. By way of example, this description can be implemented by virtue of capturing the centroid coordinates of floaters in 3-D, decomposing the latter in terms of structure into triangles whose edges are mathematically described by way of graphs, that is to say connection descriptions. This description allows methodical processing of floaters, even if these change their relative positions, for as long as the neighborhood relations are maintained or can be updated.

During the treatment, dynamic tracking of (identification of selected and non-selected) floaters is moreover realizable for the purposes of applying the selection criteria even in the case of moving floaters.

If a plurality of floaters is treated in one session, it may be necessary to remove the floater residues (gas bubbles) more quickly. To this end, it is possible to realize additional incisions in the vitreous humor (vitreolysis) for the purposes of realizing areas or channels for conveying the floater residues (gas bubbles) or else for unburdening a vitreous traction. A calculation of a mechanical model of the forces acting on the retina before, during and after the incision process is possible using the proposed arrangement.

The solution according to the invention provides an arrangement for OCT-assisted laser treatment of vitreous humor opacification, which rectifies the disadvantages of the known technical solutions.

The arrangement facilitates a simpler, quicker and especially safer treatment of bothersome vitreous humor opacification by way of laser vitreolysis. Moreover, the solution can easily be implemented and is economically cost-effective.

The present invention relates to an arrangement provided for sparing, low-risk laser treatment of vitreous humor opacification which is almost painless. A partly or completely automated therapy device (system) is proposed, in which an OCT system is used for navigation purposes in order to locate the floaters within the scope of the treatment and in order to assist the treatment thereby.

The proposed arrangements also facilitate the safer treatment of hard to recognize, largely transparent floaters that change their position, with the latter no longer having to be performed manually and a long-winded positioning of the processing laser beam by application of a visible (blinding) target laser beam no longer being mandatory.

The risk of retinal damage as a result of incorrect focal positions or a distance between laser focus and sensitive structures of the eye that is too small could be removed by the determination of exclusion criteria for the treatment.

Moreover, the risk of retinal damage in the case of incomplete vitreous humor detachment as a result of a local increase of the pull on the retina could be reduced by virtue of the treatment being adapted or terminated on account of derived abort criteria.

The present invention may be embodied in other specific forms without departing from the spirit of the essential attributes thereof, therefore, the illustrated embodiments should be considered in all respects as illustrative and not restrictive, reference being made to the appended claims rather than to the foregoing description to indicate the scope of the invention.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of U.S.C. § 112(f) are not to be invoked unless the specific terms "means for" or "step for" are recited in a claim.

The invention claimed is:

1. An OCT-assisted laser vitreolysis arrangement for an eye, comprising:
an OCT (Optical Coherence Tomography) system;
a laser system with deflection unit, a treatment beam and at least one pilot beam that facilitates monitoring a correspondence of a treatment beam focus and a target area;
optical elements that couple the OCT system and laser system; and
a display unit and a central control and operating unit;
wherein the OCT system is configured to locate floaters and is further configured to simultaneously detect scattered light of the pilot beam;
wherein the laser system is configured to destroy the floaters by application of laser pulses; and
wherein the central control and operating unit is configured to determine a distance of the floaters located from structures of the eye in addition to coordinates of the floaters located and configured to derive exclusion criteria for treatment, and configured to align the deflection unit of the laser system on these coordinates and to focus and activate the laser system.

2. The arrangement as claimed in claim 1, wherein the central control and operating unit is configured to determine the type, geometry or both of the floaters in addition to the coordinates thereof, and to generate or select application-specific irradiation patterns for the laser system therefrom.

3. The arrangement as claimed in claim 1, wherein the central control and operating unit is configured to determine changes in structures of the eye closest to the floater located during the treatment and to derive abort or exclusion criteria for the treatment.

4. The arrangement as claimed in claim 3, wherein the central control and operating unit is configured to automatically trigger within a time period of <5 ms following detection of a floater, taking account of derived abort or exclusion criteria for the treatment and generated or selected application-specific irradiation patterns.

5. The arrangement as claimed in claim 1, wherein the optical elements that couple the OCT system and the laser system comprise dichroic or polarization-sensitive components or use a geometric combination.

6. The arrangement as claimed in claim 1, wherein the display unit further comprises eyepieces, a visual display unit or both.

7. The arrangement as claimed in claim 6, further comprising a tracking unit that tracks an irradiation pattern and wherein tracking of the irradiation pattern is displayed in the eyepieces, on the display or both.

8. The arrangement as claimed in claim 1, wherein the OCT system, the laser system with deflection unit, the optical elements for coupling OCT system and laser system, the display unit and the central control and operating unit are integrated in a slit lamp biomicroscope.

9. The arrangement as claimed in claim 1, wherein the OCT system is based on a spectral domain method or time domain method or a swept source method.

10. The arrangement as claimed in claim 1, wherein the OCT system is configured as a one-, two- or three-dimensionally scanning system.

11. The arrangement as claimed in claim 1, wherein the OCT system has a sensitivity of at least 90 dB over an entire A scan.

12. The arrangement as claimed in claim 1, wherein the OCT system attains a sensitivity of 90 dB at most sensitive point in an A scan.

13. The arrangement as claimed in claim 1, wherein the laser system includes a us-laser, an ns-laser, a ps-laser, an fs-laser or a combination thereof.

14. The arrangement as claimed in claim 1, wherein the at least one pilot beam of the laser system comprises a continuous or quasi-continuous pilot beam.

15. The arrangement as claimed in claim 1, wherein the at least one pilot beam of the laser system has a wavelength in a visible or an infrared spectral range.

16. The arrangement as claimed in claim 1, wherein a difference in the wavelengths of the OCT system and the laser system is <50 nm.

17. The arrangement as claimed in claim 1, further comprising a fixation mark visible to the patient to facilitate advantageous or deliberate positioning of the eye.

18. The arrangement as claimed in claim 1, further comprising a vacuum contact glass that facilitates fixating the eye.

19. The arrangement as claimed in claim 1, wherein the OCT system has an axial resolution that is higher than a smallest Rayleigh length of the laser system utilized.

20. The arrangement as claimed in claim 1, wherein the OCT has a first numerical aperture that is smaller in comparison with a second numerical aperture of the laser.

21. The arrangement as claimed in claim 1, wherein prior to treatment the central control and operating unit is designed to map the floaters and based thereon plan the treatment.

22. An OCT-assisted laser vitreolysis arrangement for an eye, comprising:
   an OCT (Optical Coherence Tomography) system;
   a laser system with deflection unit;
   optical elements that couple the OCT system and laser system; and
   a display unit and a central control and operating unit;
   wherein the OCT system is configured to locate individual floaters;
   wherein the laser system is configured to destroy the floaters by application of laser pulses; and
   wherein the central control and operating unit is
   configured to determine a distance of the floaters located from structures of the eye in addition to coordinates of the floaters located and
   configured to derive exclusion criteria for treatment, and
   configured to determine a geometry of the floaters in addition to the coordinates thereof and to generate or choose application-specific irradiation patterns for the laser system based on the geometry of the floaters, and
   configured to align the deflection unit of the laser system on these coordinates and to focus and activate the laser system.

23. The OCT-assisted laser vitreolysis arrangement as claimed in claim 22, wherein central control and operating unit is designed to automatically trigger the laser treatment within a time period selected from a group consisting of <20 ms, <10 ms and <5 ms, taking account of the derived exclusion criteria for the treatment and the generated or chosen application-specific irradiation patterns.

24. An OCT-assisted laser vitreolysis arrangement for an eye, comprising:
   an OCT (Optical Coherence Tomography) system;
   a laser system with deflection unit;
   optical elements that couple the OCT system and laser system;
   a display unit and a central control and operating unit; and
   a tracking unit that tracks an irradiation pattern and wherein tracking of the irradiation pattern is displayed in the eyepieces, on the display or both;
   wherein the OCT system is configured to locate floaters and the tracking unit is configured to track the floaters individually as the floaters move;
   wherein the laser system is configured to destroy the floaters by application of laser pulses; and
   wherein the central control and operating unit is configured to determine a distance of the floaters located from structures of the eye in addition to coordinates of the floaters located and configured to derive exclusion criteria for treatment, and configured to align the deflection unit of the laser system on these coordinates and to focus and activate the laser system.

* * * * *

UNITED STATES PATENT AND TRADEMARK OFFICE
CERTIFICATE OF CORRECTION

PATENT NO. : 12,295,885 B2
APPLICATION NO. : 17/766607
DATED : May 13, 2025
INVENTOR(S) : Hacker et al.

Page 1 of 1

It is certified that error appears in the above-identified patent and that said Letters Patent is hereby corrected as shown below:

In the Specification

Column 5, Line 54, delete "450" and insert --45°--

Column 8, Line 45, delete "Fourier domain mode locked (FDML)" and insert --Fourier domain mode locking (FDML--

Column 11, Line 61, delete "thereof," and insert --thereof;--

Column 12, Line 43, delete "U.S.C." and insert --35 U.S.C.--

In the Claims

Column 13, Line 48, delete "us-laser" and insert --μs-laser--

Column 14, Line 26, delete "located and" and insert --located, and--

Signed and Sealed this
Second Day of September, 2025

Coke Morgan Stewart
*Acting Director of the United States Patent and Trademark Office*